United States Patent
Kim et al.

(10) Patent No.: US 11,385,449 B2
(45) Date of Patent: Jul. 12, 2022

(54) GALVANOMETER SCANNER AND PHOTOACOUSTIC MICROSCOPE SYSTEM HAVING THE SAME

(71) Applicant: POSTECH ACADEMY-INDUSTRY FOUNDATION, Pohang-si (KR)

(72) Inventors: Chul Hong Kim, Pohang-si (KR); Jin Young Kim, Pohang-si (KR); Jong Beom Kim, Yangsan-si (KR); Jin Woo Baik, Daejeon-si (KR)

(73) Assignee: POSTECH ACADEMY-INDUSTRY FOUNDATION, Pohang-si (KR)

( * ) Notice: Subject to any disclaimer, the term of this patent is extended or adjusted under 35 U.S.C. 154(b) by 353 days.

(21) Appl. No.: 16/477,181

(22) PCT Filed: Oct. 4, 2018

(86) PCT No.: PCT/KR2018/011728
§ 371 (c)(1),
(2) Date: Jul. 10, 2019

(87) PCT Pub. No.: WO2020/045729
PCT Pub. Date: Mar. 5, 2020

(65) Prior Publication Data
US 2021/0333530 A1    Oct. 28, 2021

(30) Foreign Application Priority Data
Aug. 28, 2018 (KR) .................. 10-2018-0101070

(51) Int. Cl.
*G02B 21/00* (2006.01)
*G02B 26/10* (2006.01)

(52) U.S. Cl.
CPC ..... *G02B 21/0052* (2013.01); *G02B 21/0048* (2013.01); *G02B 26/105* (2013.01)

(58) Field of Classification Search
CPC ........ G02B 21/02; G02B 21/24; G02B 21/00; G02B 21/0012; G02B 21/0076; G02B 21/365; G02B 21/367; G02B 21/16; G02B 21/26; G02B 21/06; G02B 21/248; G02B 21/33; G02B 21/361; G02B 21/0008;
(Continued)

(56) References Cited

U.S. PATENT DOCUMENTS 5,920,756 A * 7/1999 Matsuda ............ G03G 7/0006
399/307
8,081,362 B2  12/2011 El-Rifai
(Continued)

FOREIGN PATENT DOCUMENTS

JP    H08-192286 A1    7/1996
JP    2013-078771 A    5/2013
(Continued)

*Primary Examiner* — William R Alexander
*Assistant Examiner* — Sharrief I Broome
(74) *Attorney, Agent, or Firm* — Morgan, Lewis & Bockius LLP

(57) ABSTRACT

The present invention relates to a galvanometer scanner, and the galvanometer scanner includes a mirror mounting shaft having a portion inserted into a shaft insertion opening of a housing which includes the shaft insertion opening on one surface thereof and has contents contained therein; and a mirror mounted at the mirror mounting shaft and positioned inside the housing.

20 Claims, 8 Drawing Sheets

(58) Field of Classification Search
CPC ............ G02B 21/0032; G02B 21/0088; G02B 21/04; G02B 21/0016; G02B 21/241; G02B 13/22; A61B 90/20; A61B 1/00188; A61B 1/002; A61B 34/30; A61B 3/0075; A61B 5/0075; A61B 90/25; A61B 1/00096; A61B 1/00149; A61B 1/00195; A61B 1/015; A61B 1/043; A61B 1/0638; A61B 1/313; A61B 2017/00199; A61B 2017/00207; A61B 2017/00725; A61B 2034/2055; A61B 2034/2059; A61B 2090/0813

See application file for complete search history.

(56) References Cited

U.S. PATENT DOCUMENTS

| | | | | |
|---|---|---|---|---|
| 2005/0111089 A1* | 5/2005 | Baer | ............ | G02B 21/0076 |
| | | | | 359/368 |
| 2006/0250687 A1* | 11/2006 | Karaki | ............ | G02B 21/02 |
| | | | | 359/368 |
| 2011/0254948 A1* | 10/2011 | Eisfeld | ............ | A61P 43/00 |
| | | | | 348/135 |
| 2017/0020015 A1* | 1/2017 | Koepsell | ............ | H02K 5/10 |

FOREIGN PATENT DOCUMENTS

| | | |
|---|---|---|
| KR | 10-1156843 B1 | 2/2011 |
| KR | 10-1517971 B1 | 5/2015 |
| KR | 10-1749602 B1 | 6/2017 |
| KR | 10-1852560 B1 | 4/2018 |

\* cited by examiner

GALVANOMETER SCANNER AND PHOTOACOUSTIC MICROSCOPE SYSTEM HAVING THE SAME

TECHNICAL FIELD

The present invention relates to a galvanometer scanner and a photoacoustic microscope system having the same.

BACKGROUND ART

The photoacoustic microscope system irradiates a portion of a target to be inspected with a laser beam and subsequently measures ultrasound generated according to the amount of laser beam absorbed to the target to thus acquire a three-dimensional (3D) image of the intended portion of the target.

In the photoacoustic microscope system, generally, light irradiated to the target and ultrasound generated from the target are matched in focus in the same path to maximize measurement sensitivity of a photoacoustic signal.

In order to match light and ultrasound in focus in a single path, additional devices such as photo-acoustic couplers may be used or a ring transducer having a hole in a middle portion thereof among ultrasonic transducers is used.

Since ultrasound has good transmission efficiency in a liquid such as water or an ultrasound gel, ultrasound is collected mainly in water or the ultrasound gel.

Thus, the components such as an ultrasonic transducer and an opto-ultrasonic coupler for collecting ultrasound are mainly positioned in water or in gel. In general, a linear stage based on a step motor is used to scan two-dimensionally the ultrasonic transducer or the opto-ultrasonic coupler positioned in water but a total image rate of a photoacoustic microscope is low due to a low scanning speed.

Galvanometer scanners having characteristics of scanning light by accurate responsiveness, fast mobility, and the like, based on various input signals such as a sinusoidal wave and a triangular wave have been widely used in optical image scanning devices such as optical coherence tomography (OCT), two-photon microscopes, and the like.

A photoacoustic microscope using the galvanometer scanner may scan a target using only light in the air to acquire an image of the intended target, but in this case, measurement sensitivity of the target is low, thus being limited in use.

Therefore, in order to increase measurement sensitivity, the photoacoustic microscope uses ultrasound as well as light in many cases, and in this case, it is necessary to scan the target simultaneously using light and ultrasound while maintaining coaxial confocal, for which a motor is used.

However, the galvanometer scanner using a motor is vulnerable to moisture due to the use characteristics of the motor, and thus, it may not be used in water which is a medium for transmitting ultrasound. As a result, the photoacoustic microscope system scanning both ultrasound and light has many limitations in using such a galvanometer scanner.

RELATED ART DOCUMENT

Korean Patent Registration No. 10-1156843 (Published on Jun. 18, 2012, Entitled "Galvanometer Scanner")

DISCLOSURE

Technical Problem

An aspect of the present invention is to scan light and ultrasound in a fluid such as water using a galvanometer scanner.

Another aspect of the present invention is to improve measurement sensitivity of a photoacoustic microscope system including a galvanometer scanner.

Another aspect of the present invention is to improve an image display speed of a photoacoustic microscope system including a galvanometer scanner.

Technical Solution

According to an aspect of the present invention, there is provided a galvanometer scanner including: a mirror mounting shaft having a portion inserted into a shaft insertion opening of a housing which includes the shaft insertion opening on one surface thereof and has contents contained therein; and a mirror mounted at the mirror mounting shaft and positioned inside the housing.

The mirror mounting shaft and the housing may be formed of a hydrophobic material.

The galvanometer scanner according to the above features may further include a sealing member inserted into the mirror mounting shaft and mounted at the shaft insertion opening.

The galvanometer scanner according to the above features may further include a waterproof agent filling a space between the shaft insertion opening and a portion of the mirror mounting shaft inserted into the shaft insertion opening.

The galvanometer scanner according to the above features may further include a waterproof case surrounding the galvanometer scanner excluding the mirror and a portion of the mirror mounting shaft.

The shaft insertion opening may be positioned on an upper surface of the housing, and the mirror mounting shaft may be inserted into the shaft insertion opening perpendicular to an installation surface.

The shaft insertion opening may be positioned on the upper surface of the housing, and the mirror mounting shaft may be inserted into the shaft insertion opening slopingly at a predetermined angle with respect to the installation surface.

The shaft insertion opening may be positioned on a side surface of the housing, and the mirror mounting shaft may be inserted into the shaft insertion opening in parallel to the installation surface.

The mirror may have a flat surface or an inclined surface.

The galvanometer scanner according to the above features may further include a motor part including a motor having a motor rotating shaft mounted on the mirror mounting shaft.

In another aspect, a photoacoustic microscope system includes a galvanometer scanner;
a laser generator generating and outputting a laser beam; and a ring transducer positioned at a rear stage of the laser generator, outputting the laser beam output from the laser generator toward the galvanometer scanner and outputting ultrasound input from the galvanometer scanner, wherein the galvanometer scanner includes: a mirror mounting shaft having a portion inserted into a shaft insertion opening of a housing which includes the shaft insertion opening on one surface thereof and has contents contained therein; and a mirror mounted at the mirror mounting shaft and positioned inside the housing.

The mirror mounting shaft and the housing may be formed of a hydrophobic material.

The galvanometer scanner according to the above features may further include a sealing member inserted into the mirror mounting shaft and mounted on the shaft insertion opening.

The galvanometer scanner according to the above features may further include a waterproof agent filling a space between the shaft insertion opening and the mirror mounting shaft portion inserted into the shaft insertion opening.

The galvanometer scanner according to the above features may further include a waterproof case surrounding the galvanometer scanner excluding the mirror and a portion of the mirror mounting shaft.

The shaft insertion opening may be positioned on an upper surface of the housing, and the mirror mounting shaft may be inserted into the shaft insertion opening perpendicular to an installation surface.

The shaft insertion opening may be positioned on the upper surface of the housing, and the mirror mounting shaft may be inserted into the shaft insertion opening slopingly at a predetermined angle with respect to the installation surface.

The shaft insertion opening may be positioned on a side surface of the housing, and the mirror mounting shaft may be inserted into the shaft insertion opening in parallel to the installation surface.

The mirror may have a flat surface or an inclined surface.

Advantageous Effects

According to the present invention, the galvanometer scanner takes waterproof measures to cope with water leakage using at least one of a sealing member, a waterproof agent, a hydrophobic material, and a waterproof case.

Therefore, the galvanometer scanner of the present embodiment performs an scanning operation on a target by a transmission operation of a laser beam and a transmission operation of ultrasound through a fluid contained in a housing.

Therefore, since the photoacoustic microscope system having the galvanometer scanner of this embodiment performs an operation of acquiring a scanned image in a state in which a laser beam and ultrasound are matched in focus in the same path, and thus, efficiency of image acquisition is enhanced.

Also, since the photoacoustic microscope system acquires a scanned image by acquiring ultrasound transmitted through a fluid having good transmission efficiency of the ultrasound, efficiency of acquiring ultrasound is significantly improved.

Thus, sharpness of the scanned image, which is an image of a scanned portion of a target, is improved, and accordingly, sensitivity of the photoacoustic microscope system is also improved.

In addition, the scanned image of the target is acquired, while maintaining high sensitivity by matching the laser beam and ultrasound transmitted in a fluid in focus in the same path using the galvanometer scanner operating in the fluid.

As a result, an image acquisition speed of the photoacoustic microscope system which acquires an ultrasound signal using the galvanometer scanner is enhanced, thereby improving user's satisfaction.

DESCRIPTION OF DRAWINGS

FIGS. 6 and 7 are views illustrating an example of a mirror mounted on a galvanometer scanner according to an embodiment of the present invention, in which FIG. 6 is a view illustrating a mirror having a flat surface and FIG. 7 is a view illustrating a mirror having a inclined surface.

FIGS. 8 and 9 are views illustrating a case where a galvanometer scanner according to an embodiment of the present invention is inserted through a side surface of a housing and disposed parallel to an installation surface, in which FIG. 8 illustrates a case where a mirror having a flat surface is mounted and FIG. 9 illustrates a case where a mirror having a inclined surface is mounted.

FIGS. 10 to 12 are views illustrating a case where a galvanometer scanner according to an embodiment of the present invention is installed to penetrate through an upper surface of a housing, in which FIG. 10 is a view illustrating a case where a galvanometer scanner equipped with a mirror having a flat surface is positioned perpendicular to an installation surface, FIG. 11 illustrates a case where a galvanometer scanner equipped with a mirror having a inclined surface is positioned perpendicular to the installation surface, and FIG. 12 illustrates a case where a galvanometer scanner equipped with a mirror having a inclined surface is positioned slopingly at a predetermined angle with respect to an installation surface.

BEST MODES

Hereinafter, embodiments of the present invention will be described in detail with reference to the accompanying drawings. In describing the present invention, if it is determined that a detailed description of known functions and components associated with the present invention unnecessarily obscure the gist of the present invention, the detailed description thereof will be omitted. The terms used henceforth are used to appropriately express the embodiments of the present invention and may be altered according to a person of a related field or conventional practice. Therefore, the terms should be defined on the basis of the entire content of this specification.

Technical terms used in the present specification are used only in order to describe specific exemplary embodiments rather than limiting the present invention. The terms of a singular form may include plural forms unless referred to the contrary. It will be further understood that the terms "comprise" and/or "comprising," when used herein, specify the presence of stated features, integers, steps, operations, elements, and/or components, but do not preclude the presence or addition of one or more other features, regions, integers, steps, operations, elements, components, and/or groups thereof.

Hereinafter, a galvanometer scanner according to an embodiment of the present invention and a photoacoustic microscope system having the same will be described with reference to the accompanying drawings.

The photoacoustic microscope system having a galvanometer scanner according to an embodiment of the present invention will be described with reference to FIGS. 1 to 3.

Figure 1:
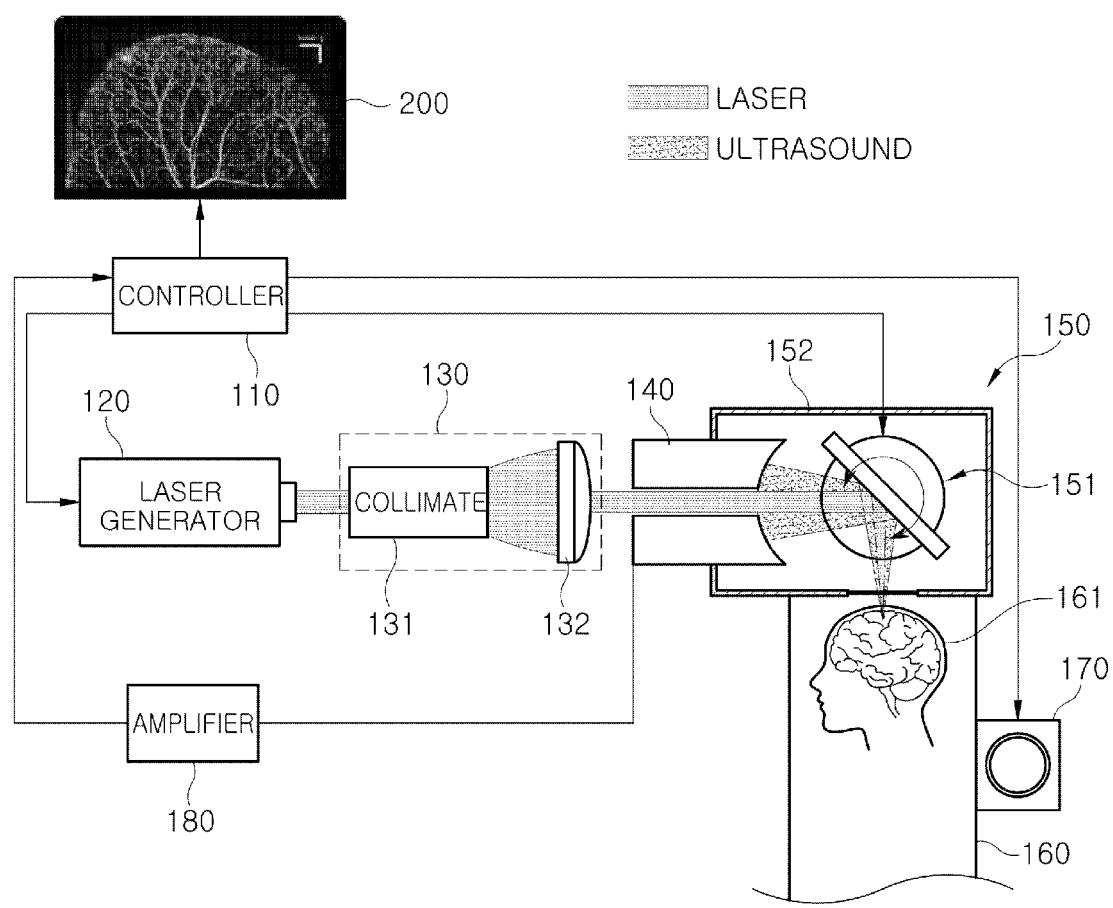
FIG. 1 is a schematic block diagram of a photoacoustic microscope system according to an embodiment of the present invention.

As illustrated in FIG. 1, the photoacoustic microscope system 1 of the present embodiment includes a controller 110, a laser generator 120 connected to the controller 110, an optical system 130 positioned at a rear stage of the laser generator 120, a ring transducer 140 positioned at a rear stage of the optical system 130, a galvanometer scanner device 150 including a galvanometer scanner 151 positioned at a front stage of the ring transducer 140, a stage 160 positioned adjacent to the galvanometer scanner device 150 such that a target 161 to be scanned is positioned, a position adjusting unit 170 connected to the stage 160, an amplifier 180 positioned at a rear stage of the ring transducer 140, and an image output unit 200 connected to the controller 110.

The controller 110, which controls an overall operation of the photoacoustic microscope system 1, is connected to the laser generator 120, the galvanometer scanner device 150, the position adjusting unit 170, the amplifier 180, and the image output unit 200 to control operations thereof.

The controller 110 controls the operations of the laser generator 120, the galvanometer scanner device 150, and the position adjusting unit 170 by outputting control signals of corresponding states to the laser generator 120, the galvano scanner device 150, and the position adjusting unit 170, respectively.

The controller 110 receives an ultrasound signal applied from the amplifier 180, processes the received ultrasound signal, and outputs the ultrasound signal to the image output unit 200 so that a state of the target 161 may be visually checked.

As described above, the laser generator 120 operates in response to a control signal from the controller 110 connected thereto to irradiate a laser beam toward the optical system 130.

In this example, the laser generated by the laser generator 120 may be a pulse laser such as a Q-switched Nd: YAG laser (532 nm, 1064 nm), a dye laser (500 nm to 650 nm), a Ti: Sapphire laser (700 nm to 900 nm) Pulsed laser.

The optical system 130 positioned at the rear stage of the laser generator 120 converts the laser output from the laser generator 120 and outputs the converted laser to the ring transducer 140. The optical system 130 includes a collimator 131 and an objective lens 132 positioned at a rear stage of the collimator 131.

The collimator 131 receives the laser beam output from the laser generator 120, converts the laser beam into a luminous flux having a predetermined magnitude, and outputs the same toward the objective lens 132.

The laser beam output from the collimator 131 is incident on the objective lens 132 and the laser beam passing through the objective lens 132 is irradiated toward the ring transducer 140.

In this example, the optical system may be a free space optical system but is not limited thereto and an optical fiber optical system using an optical fiber may be used in an alternative example.

The ring transducer 140 is a transducer having a ring-shaped planar shape with a through hole formed at a central portion thereof.

The ring transducer 140 transmits the laser beam incident from the objective lens 132 to the galvanometer scanner device 150, receives ultrasound output from the galvanometer scanner device 150, and outputs the received ultrasound toward the amplifier 180.

Accordingly, the laser beam exiting from the objective lens 132 is incident on the galvanometer scanner device 150 through the through hole of the ring transducer 140 as described above.

The galvanometer scanner device 150 of the present embodiment includes the galvanometer scanner 151 and a housing 152 in which a part of the galvanometer scanner 151 is inserted as described above.

Here, the housing 152 has a hexahedral shape, and water or a fluid (e.g., an ultrasonic gel) other than water for improving efficiency of ultrasound acquisition is contained in the housing 152.

One side of the housing 152 is at least partially open so that a portion of a mirror mounting shaft 1512 is inserted through the open portion of the corresponding side of the housing 152 so that a mirror 1513 is positioned in the water or a flow velocity in the housing 152.

A surface of the housing 152, which faces the target 161 on which A scanning operation is performed, has a thickness smaller than the other surfaces for transmission of the laser beam and ultrasound and is formed of a transparent material allowing the laser beam and ultrasound to be transmitted therethrough.

Figure 2:
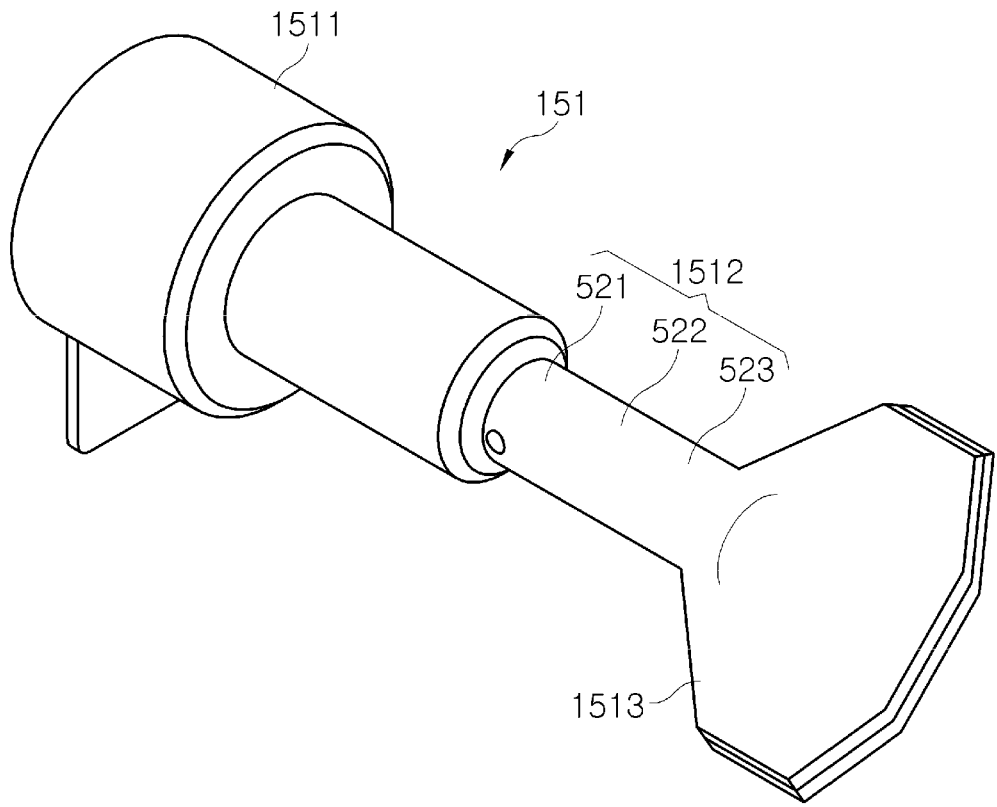
FIG. 2 is a partial perspective view of a galvanometer scanner used in a photoacoustic microscope system of FIG. 1.
Figure 3:
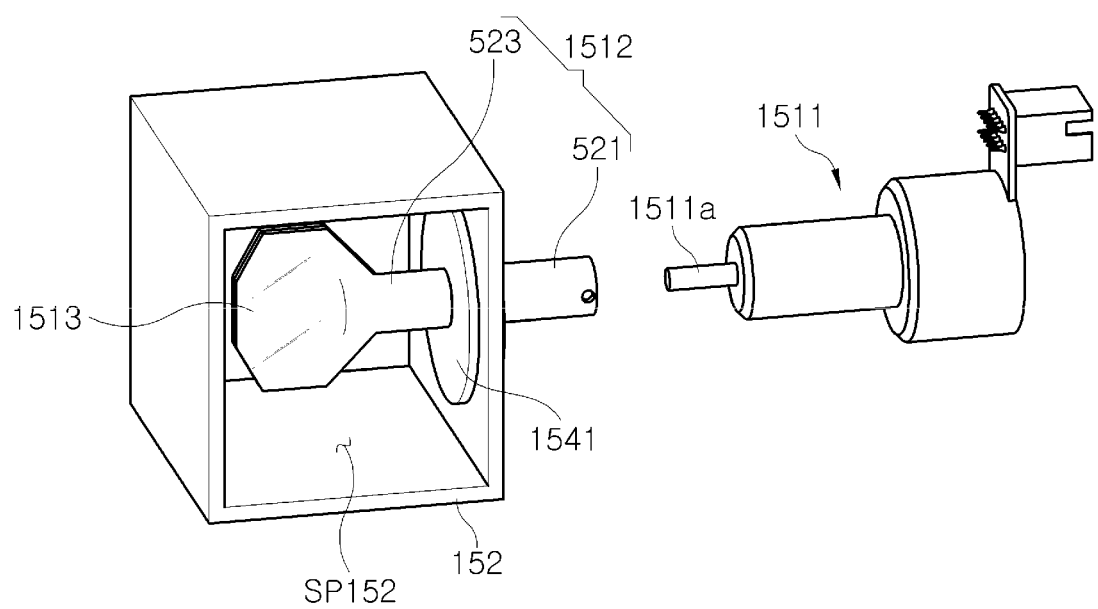
FIG. 3 is a view illustrating a state in which a galvanometer scanner according to an embodiment of the present invention is installed in a housing and one side of the housing is open for convenience of illustration.

As illustrated in FIGS. 2 and 3, the galvanometer scanner 151 includes a motor part having a motor connected to a motor rotating shaft 1511a and a motor driving unit for operating the motor, a mirror mounting shaft 1512 inserted into the motor rotating shaft 1511a so as to be connected thereto, and a mirror 1513 mounted on the mirror mounting shaft 1512.

Here, only the entirety of the mirror 1513 and a portion of the mirror mounting shaft 1512 are inserted into the housing 152 and positioned in the contents (i.e., water or ultrasonic gel) contained in the housing 152.

In this state, the motor of the galvanometer scanner 151 vibrates and rotates in a reciprocating manner, while maintaining a predetermined angle (i.e., within 20 degrees) according to an operation of the motor driving unit built in the motor part 1511, and due to the rotating operation of the motor, the motor rotating shaft 1511a connected to the motor also vibrates and rotates in a reciprocating manner, while maintaining a predetermined angle, in the same state as that of the motor.

Therefore, the mirror mounting shaft 1512 on which the mirror 1513 is mounted is also rotated according to the rotation of the motor rotating shaft 1511a to finally rotate the mirror 1513 to a desired angle in a desired direction and at a desired speed.

The mirror mounting shaft 1512 inserted into the motor rotating shaft 1511a so as to be connected to the motor rotating shaft 1511a has the mirror 1513 mounted at an end portion thereof as described above.

The mirror mounting shaft 1512 includes a first portion 521 having a shaft mounting recess (not shown) into which the motor rotating shaft 1511a is inserted and exposed to the outside, a second portion 522 continuously connected to the first portion 521 and positioned in a corresponding surface of the housing 152, i.e., a surface where the shaft insertion opening of the housing 152 is positioned, and a third portion 523 continuously connected to the second portion 522 and positioned in the housing 152.

Accordingly, one side of the first portion 521 is inserted into the motor rotating shaft 1511a so as to be connected to the motor rotating shaft 1511a. Here, a cross-section of the shaft mounting recess and the motor rotating shaft 1511a may have various shapes such as a semicircular shape or a circular shape.

The mirror 1513 is mounted at an end of the third portion 523.

The first to third portions 521 to 523 of the mirror mounting shaft 1512 which are continuously connected to each other may have the same diameter, excluding an end portion, i.e., a portion of the third portion 523, where the mirror is mounted, and thus, the mirror mounting shaft 1512 may have a cylindrical shape.

Since the mirror mounting shaft 1512 is connected to the motor rotating shaft 1511a by the first portion 521 as described above, the mirror mounting shaft 1512 rotates in the same manner as the motor rotating shaft 1511a to rotate the mirror 1513 mounted at the third portion 523 of the mirror mounting shaft 1512 in the same manner, i.e., at the same speed and in the same direction in the contents inside the housing 152.

The mirror 1513 reflects the laser beam transmitted through the ring transducer 140 toward the target 161 to be scanned and reflects ultrasound output from the target 161 back toward the ring transducer 140.

Figure 6:
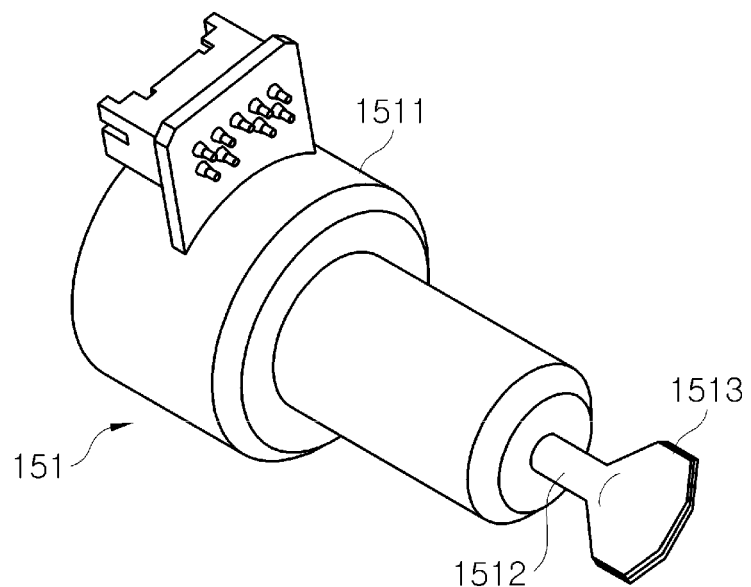
Figure 7:
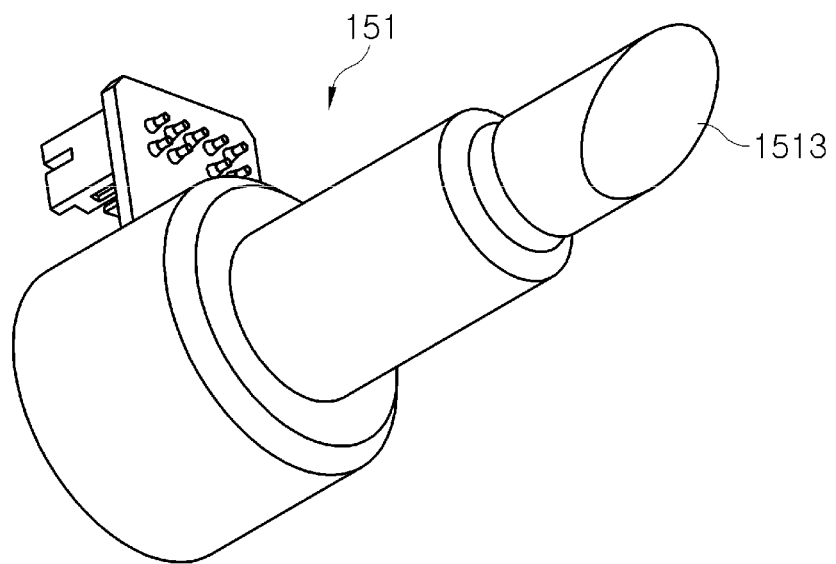

A corresponding surface of the mirror 1513 (i.e., the surface adjacent to the target 161) has a flat surface or an inclined surface as illustrated in FIGS. 6 and 7.

Here, in order to enhance reflectivity of both the laser beam and the ultrasound, the corresponding surface of the mirror 1513 may be coated with a material having high reflectivity such as aluminum (Al) or a reflector coated with the corresponding material may be additionally adhered to the corresponding surface of the mirror 1513. The reflector may be formed of silicon.

In the case of the mirror 1513 having an inclined surface, a cylindrical mirror body may be cut in a diagonal direction to form the inclined surface. Here, the angle of the inclined surface is determined according to a cutting angle.

As illustrated in FIG. 3, the housing 152 has a space SP152 in which the contents is contained in the middle portion and at least a portion of any one surface thereof is open to have the shaft insertion opening allowing the mirror mounting shaft 1512 to be rotatably inserted therethrough.

Here, in order to prevent the contents filling the housing 152 from leaking out, at least one of the various leakage preventing measures may be taken as follows.

First, as illustrated in FIG. 3, a sealing member 1541 such as an O-ring, an oil seal formed of silicone, rubber, urethane, or the like, or a waterproof bearing is inserted into the mirror mounting shaft 1512 and subsequently mounted around the shaft insertion opening, i.e., on at least one of an inner side portion and an outer side portion of the surface of the housing 152 where the shaft insertion opening is positioned.

Figure 4:
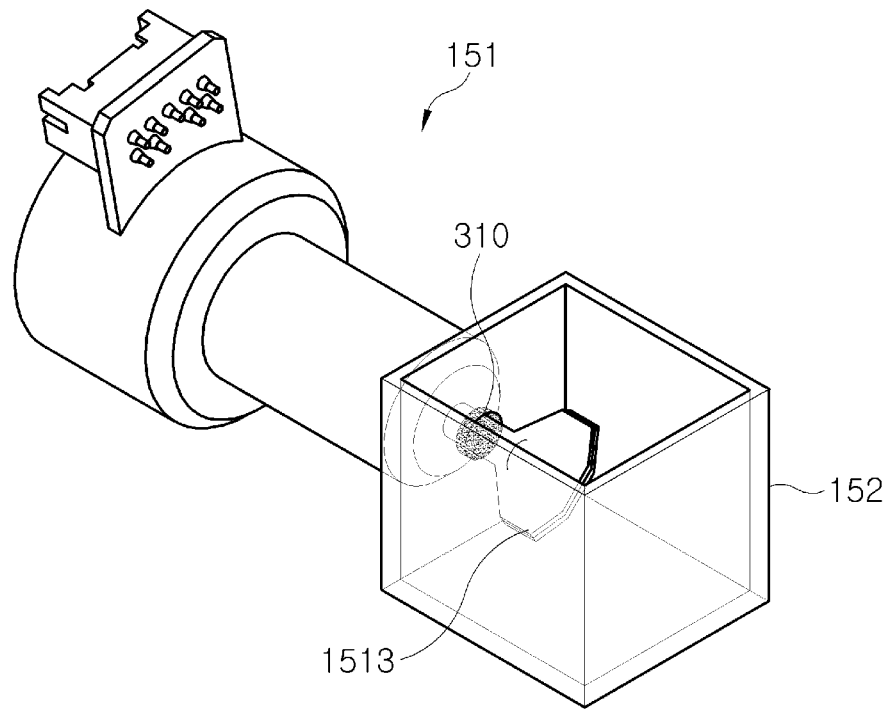
FIG. 4 is a view illustrating an example of a leakage waterproofing scheme of a galvanometer scanner according to an embodiment of the present invention, in which a waterproof agent is applied to a shaft insertion opening.

Second, as illustrated in FIG. 4, the shaft insertion opening into which the second portion 521 of the mirror mounting shaft 1512 is inserted is filled with a waterproof agent (i.e., grease) 310 in a semi-solid state such as a gal state, so that a space as a gap between an outer surface of the second portion 522 of the mirror mounting shaft 1512 and the corresponding surface of the housing 152 in contact with the shaft insertion opening is filled with the waterproof agent.

Third, as illustrated in FIG. 4, the housing 152 and the mirror mounting shaft 1512 which are in contact with the contents of the housing 152 may be formed of a hydrophobic material having hydrophobic properties (e.g., Teflon).

Figure 5:
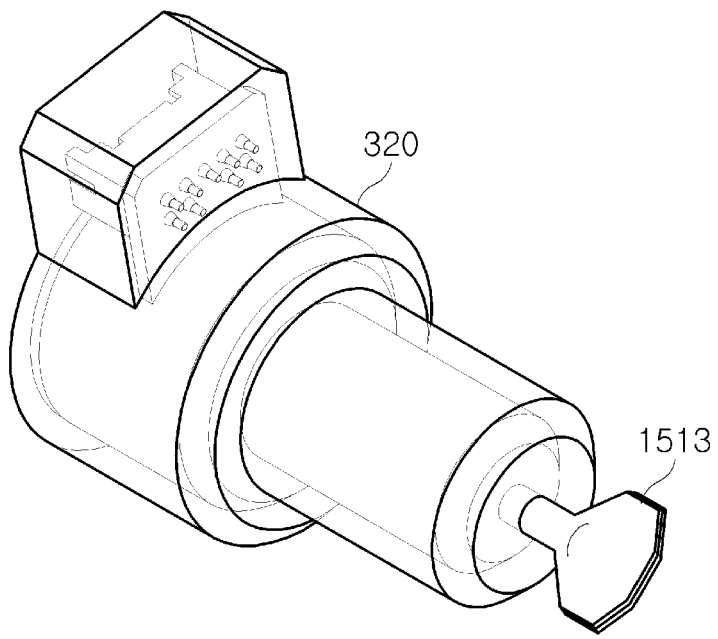
FIG. 5 is a view illustrating another example of a leakage waterproofing scheme of a galvanometer scanner according to an embodiment of the present invention, in which a waterproof case is used.

Fourth, as illustrated in FIG. 5, the galvanometer scanner 151 itself may be sealed with a waterproof case 320 having a waterproof function and then inserted into the housing 152.

The waterproof case 320 may be formed of a waterproofing synthetic resin such as vinyl or plastic.

Here, the mirror portion 1513 positioned in the housing 152 and at least a portion of the third portion 523 of the mirror mounting shaft 1512 adjacent to the mirror 1513 are not sealed by the waterproof case 320.

Further, a portion of the galvanometer scanner 151 excluding the portions 1513 and 523, which is positioned far from the housing 152, may not be sealed by the waterproof case 320.

Since the galvanometer scanner 151 employs at least one of the various leakage preventing measures of the present embodiment to prevent leakage of the contents contained in the housing 152 so as to be applied, the contents contained in the housing 152 is not leaked to the outside through the shaft insertion opening.

The galvanometer scanner 151 may be installed in the housing 152 at various angles. Here, the installation angle of the galvanometer scanner 151 is an angle with respect to an installation surface, and the installation angle may be varied according to imaging positions of the target 161 to be imaged using the galvanometer scanner 151.

Figure 8:
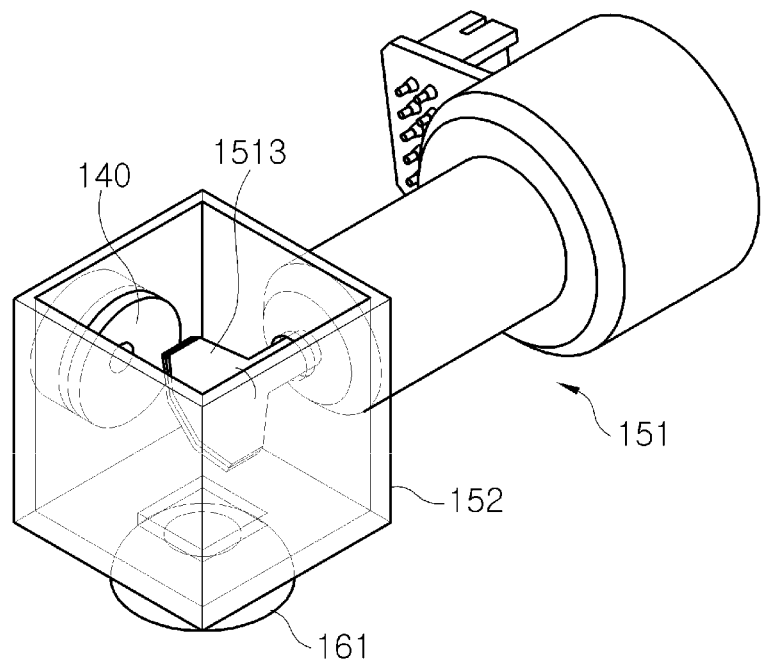
Figure 9:
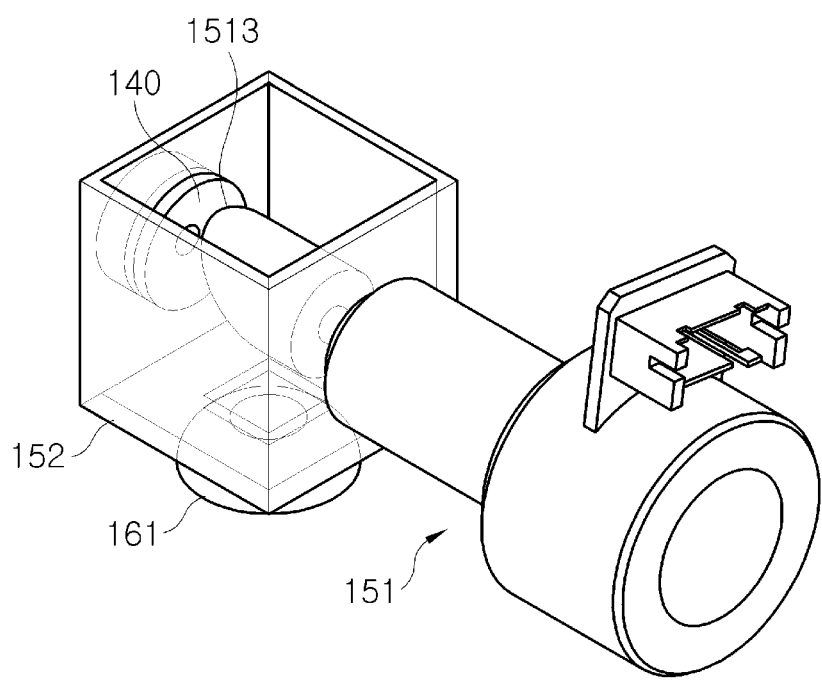

First, as illustrated in FIGS. 3, 8, and 9, the galvanometer scanner 151 is installed on one side surface of the housing 152, and in this case, the galvanometer scanner 151 is positioned in parallel to the installation surface.

When the galvanometer scanner 151 is installed parallel to the installation surface, the mirror 1513 may have a flat surface (FIGS. 3 and 8) and an inclined surface (FIG. 9). The target 161 to be imaged on the galvanometer scanner 151 is positioned below a lower surface of the housing 152.

As illustrated in FIG. 8, when the mirror 1513 has a flat surface, the galvanometer scanner 151 is positioned on a side surface immediately adjacent to a side surface on which the ring transducer 140 is set, and the mirror 1513 is positioned to face the ring transducer 140.

Accordingly, the laser beam passing through the through hole of the ring transducer 140 is reflected from the mirror 1513 and is incident on the target 161 and ultrasound output from the target 161 is reflected from the mirror 1513 and transferred to the ring transducer 140.

As illustrated in FIGS. 3, 4, and 8, when the galvanometer scanner device 150 has the mirror 1513 having a flat surface and the galvanometer scanner 151 is installed parallel to the installation surface, the galvanometer scanner 151 may scan the incident beam about twice a rotation angle (incidence-reflection) thereof, and thus, scanning efficiency of the target 161 is significantly improved.

Meanwhile, as illustrated in FIG. 9, when the mirror 1513 has an inclined surface, the galvanometer scanner 151 is positioned on a side surface opposite to the side surface on which the ring transducer 140 is set. Accordingly, the ring transducer 140 and the inclined surface of the mirror 1513 face each other on the mutually opposite sides.

Accordingly, the laser beam passing through the through hole of the ring transducer 140 is reflected from the inclined surface of the mirror 1513 positioned on the opposite side and is incident on the target 161 and ultrasound output from the target 161 is reflected from the inclined surface of the mirror 1513 and transferred to the ring transducer 140.

In this case, since the portion of the side surface of the housing 152, which is the installation surface of the housing 152, is open for installation of the galvanometer scanner 151, there is a possibility that the contents inside the housing 152 is leaked. However, in this embodiment, since at least one of the various leakage preventing measures described above is applied to the galvanometer scanner 151, leakage of contents does not occur.

As illustrated in FIG. 9, when the galvanometer scanner 151 is installed in parallel to the installation surface but has the mirror 1513 having an inclined surface, the installation angle of the galvanometer scanner 151 may be different as compared with the flat surface to facilitate installation of the galvanometer scanner 151. In addition, scanning of the laser beam or ultrasound is performed in an X-axis direction in the case of FIG. 8, whereas scanning of the laser beam or ultrasound is performed in a Y-axis direction in the case of FIG. 9.

Figure 10:
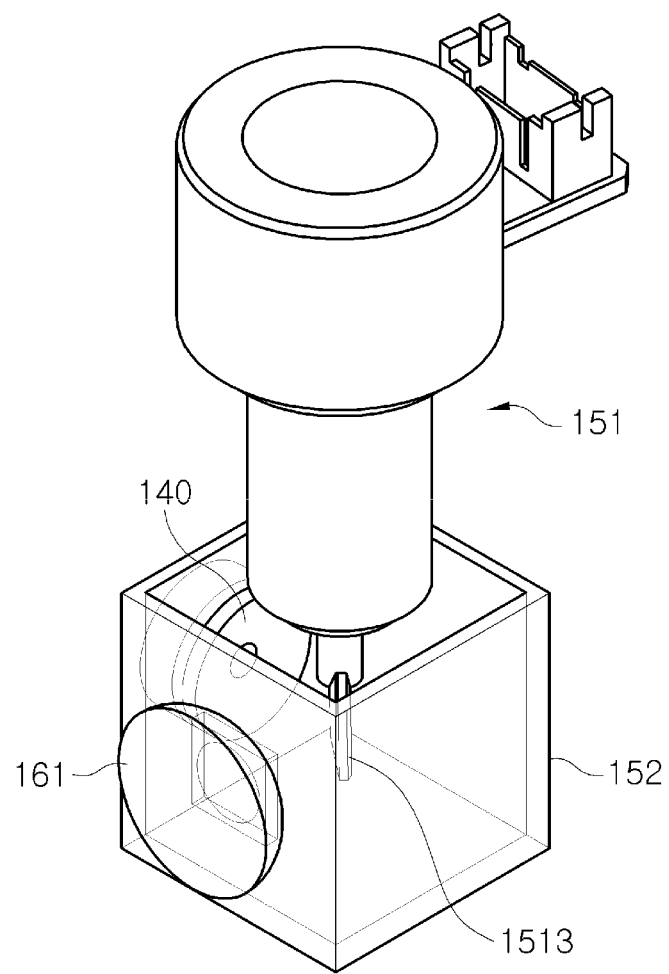
Figure 11:
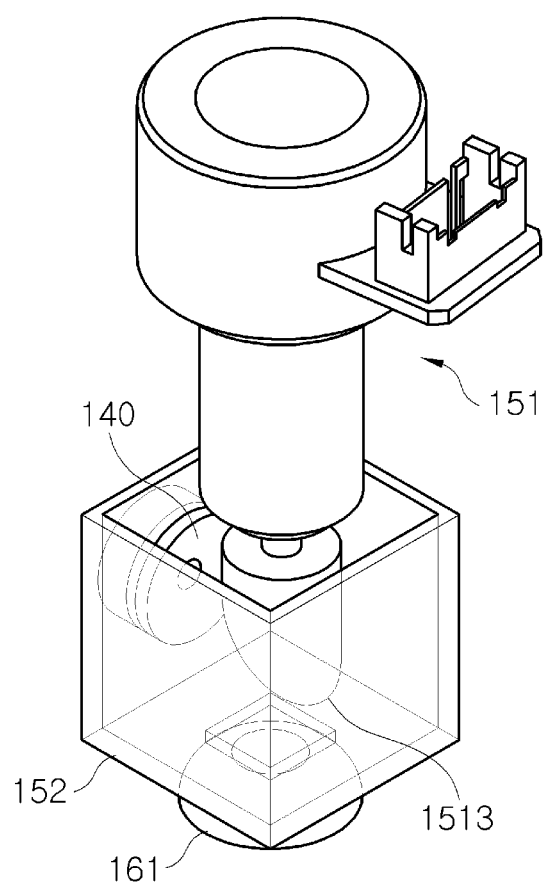
Figure 12:
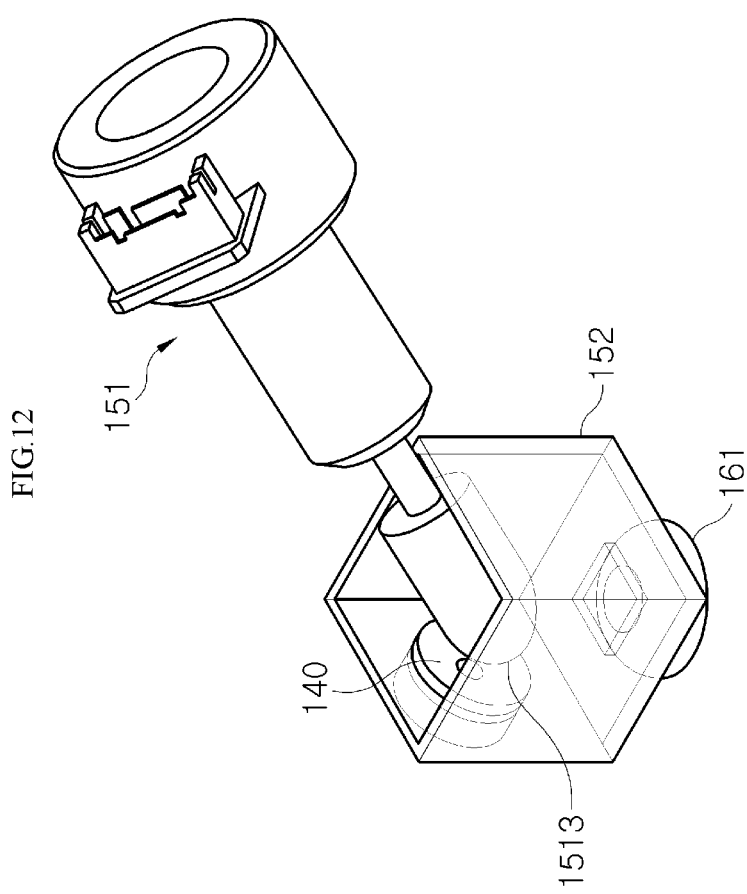

In another example, as illustrated in FIGS. 10 to 12, the galvanometer scanner 151 may be positioned on an upper surface of the housing 152.

Referring to FIGS. 10 and 11, the galvanometer scanner 151 is positioned perpendicular to the upper surface of the housing 152, and thus, the galvanometer scanner 151 is positioned perpendicular to the installation surface.

Also in this case, the mirror 1513 may have a flat surface (FIG. 10) or an inclined surface (FIG. 11).

When the mirror 1513 has the flat surface or the inclined surface as illustrated in FIGS. 10 and 11, the galvanometer scanner 151 is installed to be positioned in a direction in which the corresponding surface of the mirror 1513 faces the ring transducer 140. Accordingly, the laser beam passing through the through hole of the ring transducer 140 is reflected from the corresponding surface of the mirror 1513 facing the ring transducer 140 toward the target 161 and ultrasound output from the target 161 is reflected from the corresponding surface of the mirror 1513 so as to be transferred toward the ring transducer 140.

When the galvanometer scanner 151 is positioned perpendicular to the upper surface of the housing 152 and the mirror 1513 has the flat surface, the target 161 to be imaged may be positioned adjacent to the side surface of the housing 152, and thus, a portion of the target 161 adjacent to the corresponding side surface of the housing 152 may be imaged more efficiently.

Meanwhile, when the mirror 1513 has the inclined surface, the target 161 is positioned below the lower surface of the housing 152 and imaged.

In case where the galvanometer scanner 151 is installed on the upper surface of the housing 152, the galvanometer scanner 151 may be installed to be tilted at an angle ranging from 0 degree to 90 degrees on the installation surface as illustrated in FIG. 12 in another example.

Here, a mirror having an inclined surface may be used as the mirror 1513, and the inclined surface of the mirror 1513 is positioned to face the ring transducer 140 mounted on the housing 152. In this case, the target 161 is preferably positioned below the lower surface of the housing 152.

The laser beam passing through the through hole of the ring transducer 140 is reflected from the inclined surface of the mirror 1513 and irradiated toward the target 161 positioned on the lower side and the ultrasound output from the target 161 is reflected from the mirror 1513 and transmitted toward the ring resonator 1513.

As described above, in order to install the galvanometer scanner 151 perpendicular to the installation surface, the upper surface of the housing 152 is fully or partially open. Thus, the corresponding portion 523 of the mirror mounting shaft 1512 of the galvanometer scanner 151 having the mirror 1513 is positioned in the housing 152 through the opened upper surface.

As described above, since the upper surface of the housing 152 is open to allow the galvanometer scanner 151 to be installed perpendicular to the installation surface, the contents contained in the housing 152 is prevented from flowing out through the opened upper surface, eliminating the necessity of a separate waterproofing facility for preventing leakage of the contents.

Therefore, omission of the waterproofing facility may reduce manufacturing time and manufacturing cost of the galvanometer scanner device 150.

In addition, when the galvanometer scanner 151 is positioned on the upper surface of the housing 152, difficulty in securing a space for installing the galvanometer scanner 151 may be significantly reduced.

That is, since the portion 523 of the mirror mounting shaft 1512 where the mirror 1513 is mounted in the housing 152 is positioned perpendicular to the installation surface, the motor part 1511 connected to the mirror mounting shaft 1512 is also positioned perpendicular to the installation surface.

Therefore, since both the mirror mounting shaft 1512 and the motor part 1511 are installed in an upper space of the housing 152, an installation space for installing the mirror mounting shaft 1512 and the motor part 1511 is unnecessary.

In addition, when the galvanometer scanner 151 is installed in the structure as illustrated in FIG. 10, since the flat mirror 1513 is used, a scanning angle of the mirror 1513 is widened, and since the corresponding beam is scanned in the direction of the side surface of the housing, a lateral image of the target 161 may be acquired more easily and clearly.

In the case of FIG. 11, since the mirror 1513 having an inclined surface is used, a beam scanning operation is performed on the lower surface of the housing 152, and thus, user convenience is enhanced.

In the case of FIG. 12, as described above, since the mirror 1513 having an inclined surface is used in the same manner as in FIG. 11, the galvanometer scanner 151 may be positioned above the housing 152 and a scanning direction may be more easily changed by adjusting an angle, thereby further improving accuracy of the scanning operation with respect to the target 161.

Referring back to FIG. 1, the stage 160 is a place where the target 161 to be scanned using the laser beam reflected from the mirror 1513 of the galvanometer scanner 151 is positioned. As described above, the position of the target 161 in the stage 160 is also determined according to the installation position of the mirror 1513 of the galvanometer scanner 151.

Therefore, when the corresponding position of the target 161 is irradiated with the laser beam, the irradiated laser beam is absorbed by the irradiated portion of the target 161, and the portion of the target 161 to which the laser beam is absorbed has an increased temperature due to the influence of the absorbed laser beam and expanded, causing a thermos-elastic expansion phenomenon to occur.

Ultrasound is generated around the corresponding portion of the target 161 due to the thermos-elastic expansion phenomenon. Here, a size of the generated ultrasound signal may be determined according to the amount of the laser beam to be absorbed, i.e., the amount of the laser beam irradiated to the corresponding portion of the target 161.

As illustrated in FIG. 1, the ultrasound generated at the corresponding portion of the target 161 is output toward the mirror 1513 of the galvanometer scanner 151 and is output toward the transducer 140 due to a reflecting operation of the mirror 1513.

The position adjusting unit 170 may serve to move a position of the stage 160 in a desired direction under the control of the controller 110 and include a motor or the like.

The amplifier 180 positioned at the rear stage of the ring transducer 140 amplifies the ultrasound signal applied from the ring transducer 140 to a predetermined magnitude and outputs the amplified ultrasound signal to the controller 110.

The controller 110 generates an image signal corresponding to a scanned image according to a scanning operation of the target 161 positioned at the stage 160 using the magnitude of the input ultrasound signal and outputs the generated image signal to the image output unit 200. The image output unit 200 outputs an image corresponding to the image signal input from the controller 110 as a scanned image. So far, the galvanometer scanner and the photoacoustic microscope system using the galvanometer scanner of the present invention have been described. The present invention is not limited to the above-described embodiments and the accompanying drawings, and various modifications and changes may be made by those skilled in the art to which the present invention pertains. Accordingly, the scope of the present invention should be determined not only by the claims of the present disclosure but also by equivalents to the claims.

| | |
|---|---|
| 1: photoacoustic microscope system | 120: laser generator |
| 130: optical system | |
| 140: ring transducer | 150: galvanometer scanner device |
| 151: galvanometer scanner | 1511: motor part |
| 1512: mirror mounting shaft | 1513: mirror |
| 152: housing | 1541: sealing member |
| 160: stage | 180: amplifier |
| 521: first portion | 522: second portion |
| 523: third portion | 200: image output unit |

The invention claimed is:

1. A galvanometer scanner comprising:
   a mirror mounting shaft having a portion inserted into a shaft insertion opening of a housing which includes the shaft insertion opening on one surface thereof and has contents contained therein; and
   a mirror mounted at the mirror mounting shaft and positioned inside the housing,
   wherein:
   the shaft insertion opening is positioned on an upper surface of the housing; and
   the mirror mounting shaft is inserted into the shaft insertion opening perpendicular to an installation surface.

2. The galvanometer scanner of claim 1, further comprising:
   a waterproof agent filling a space between the shaft insertion opening and the portion of the mirror mounting shaft inserted into the shaft insertion opening.

3. The galvanometer scanner of claim 1, further comprising:
   a sealing member inserted into the mirror mounting shaft and mounted at the shaft insertion opening.

4. The galvanometer scanner of claim 1, wherein the mirror mounting shaft and the housing are formed of a hydrophobic material.

5. The galvanometer scanner of claim 1, further comprising:
   a waterproof case surrounding the galvanometer scanner excluding the mirror and the portion of the mirror mounting shaft.

6. The galvanometer scanner of claim 1, wherein the mirror has a flat surface or an inclined surface.

7. The galvanometer scanner of claim 1, further comprising:
   a motor part including a motor having a motor rotating shaft mounted on the mirror mounting shaft.

8. A photoacoustic microscope system comprising:
   a galvanometer scanner;
   a laser generator generating and outputting a laser beam; and
   a ring transducer positioned at a rear stage of the laser generator, outputting the laser beam output from the laser generator toward the galvanometer scanner, and outputting ultrasound input from the galvanometer scanner,
   wherein the galvanometer scanner includes:
   a mirror mounting shaft having a portion inserted into a shaft insertion opening of a housing which includes the shaft insertion opening and having contents contained therein; and
   a mirror mounted at the mirror mounting shaft and positioned inside the housing, wherein:
   the shaft insertion opening is positioned on an upper surface of the housing; and
   the mirror mounting shaft is inserted into the shaft insertion opening slopingly at a predetermined angle with respect to an installation surface.

9. The photoacoustic microscope system of claim 8, wherein the mirror mounting shaft and the housing are formed of a hydrophobic material.

10. The photoacoustic microscope system of claim 8, wherein
    the galvanometer scanner further includes a sealing member inserted into the mirror mounting shaft and mounted on the shaft insertion opening.

11. The photoacoustic microscope system of claim 8, wherein
    the galvanometer scanner further includes a waterproof agent filling a space between the shaft insertion opening and the mirror mounting shaft portion inserted into the shaft insertion opening.

12. The photoacoustic microscope system of claim 8, wherein
    the galvanometer scanner further includes a waterproof case surrounding the galvanometer scanner excluding the mirror and the portion of the mirror mounting shaft.

13. The photoacoustic microscope system of claim 8, wherein the mirror has a flat surface or an inclined surface.

14. An apparatus comprising:
    a mirror mounting shaft having a portion inserted into a shaft insertion opening of a housing which includes the shaft insertion opening on one surface thereof and has contents contained therein; and
    a mirror mounted at the mirror mounting shaft and positioned inside the housing,
    wherein:
    the shaft insertion opening is positioned on an upper surface of the housing; and
    the mirror mounting shaft is inserted into the shaft insertion opening perpendicular to an installation surface or is inserted into the shaft insertion opening slopingly at a predetermined angle with respect to the installation surface.

15. The apparatus of claim 14, further comprising:
a waterproof agent filling a space between the shaft insertion opening and the portion of the mirror mounting shaft inserted into the shaft insertion opening.

16. The apparatus of claim 14, further comprising:
a sealing member inserted into the mirror mounting shaft and mounted at the shaft insertion opening.

17. The apparatus of claim 14, wherein
the mirror mounting shaft and the housing are formed of a hydrophobic material.

18. The apparatus of claim 14, further comprising:
a waterproof case surrounding the apparatus excluding the mirror and the portion of the mirror mounting shaft.

19. The apparatus of claim 14, wherein the mirror has a flat surface or an inclined surface.

20. The apparatus of claim 14, further comprising:
a motor part including a motor having a motor rotating shaft mounted on the mirror mounting shaft.

* * * * *